(12) United States Patent
Hume et al.

(10) Patent No.: US 8,152,815 B2
(45) Date of Patent: Apr. 10, 2012

(54) CONSTRAINED ACETABULAR TRIALING SYSTEM

(75) Inventors: Eric L. Hume, Wynnewood, PA (US); Anthony J. Svarczkopf, Cordova, TN (US)

(73) Assignee: Wright Medical Technology, Inc., Arlington, TN (US)

(*) Notice: Subject to any disclaimer, the term of this patent is extended or adjusted under 35 U.S.C. 154(b) by 1168 days.

(21) Appl. No.: 11/928,425

(22) Filed: Oct. 30, 2007

(65) Prior Publication Data

US 2008/0109001 A1    May 8, 2008

Related U.S. Application Data

(60) Provisional application No. 60/863,462, filed on Oct. 30, 2006.

(51) Int. Cl.
*A61B 17/58* (2006.01)
*A61B 17/60* (2006.01)
*A61F 2/00* (2006.01)

(52) U.S. Cl. .......................................... 606/102; 606/91
(58) Field of Classification Search .............. 606/86 R, 606/89, 91, 99, 102; 623/22.43–22.45
See application file for complete search history.

(56) References Cited

U.S. PATENT DOCUMENTS

| | | | |
|---|---|---|---|
| 4,135,517 A | 1/1979 | Reale | |
| 4,241,463 A | 12/1980 | Khovaylo | |
| 4,798,610 A | 1/1989 | Averill | |
| 5,156,626 A | 10/1992 | Broderick | |
| 6,234,961 B1* | 5/2001 | Gray | 600/234 |
| 6,860,903 B2 | 3/2005 | Mears | |
| 2002/0116068 A1* | 8/2002 | McLean | 623/22.15 |

* cited by examiner

*Primary Examiner* — Thomas C. Barrett
*Assistant Examiner* — Andrew Yang
(74) *Attorney, Agent, or Firm* — Duane Morris LLP

(57) ABSTRACT

A trial head and shell for use in trial reduction of hip implants, and particularly bipolar implants, having locking features that prevent the head from dissociating from the shell during trialing, yet which allow the head and shell to be readily assembled and disassembled in the operating room. A cut-out region is formed in an outer bearing surface of the head. The cut-out region allows the head to pass through a trial shell opening and into the shell, yet is oriented such that when the head is associated with a femoral neck, the head cannot disassociate from the shell. Orientation indicators can be provided for use in assembly and disassembly. The trial head and associated shells can be provided in the form of a surgical kit including hip implants. Methods of use are provided.

22 Claims, 4 Drawing Sheets

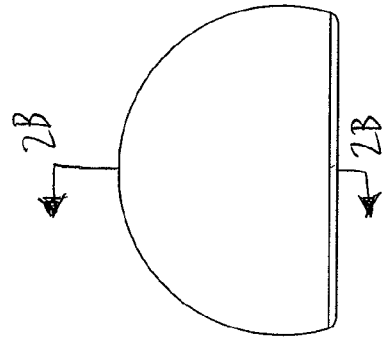
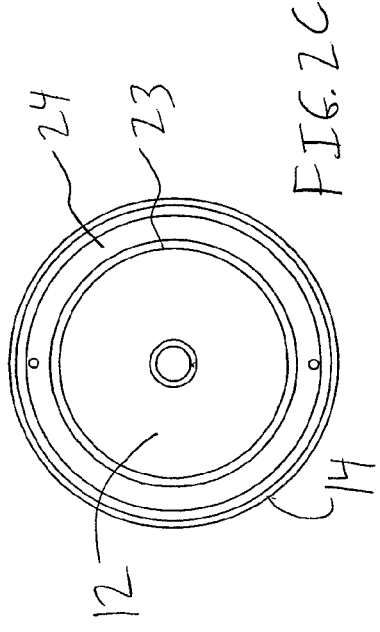
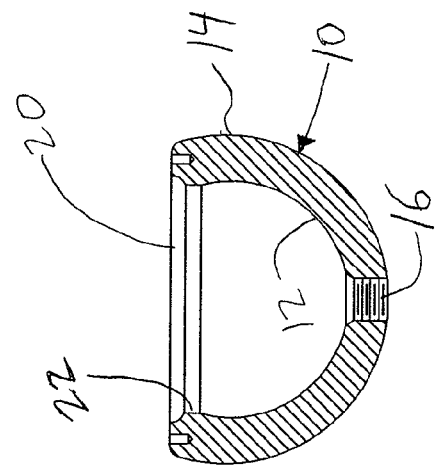

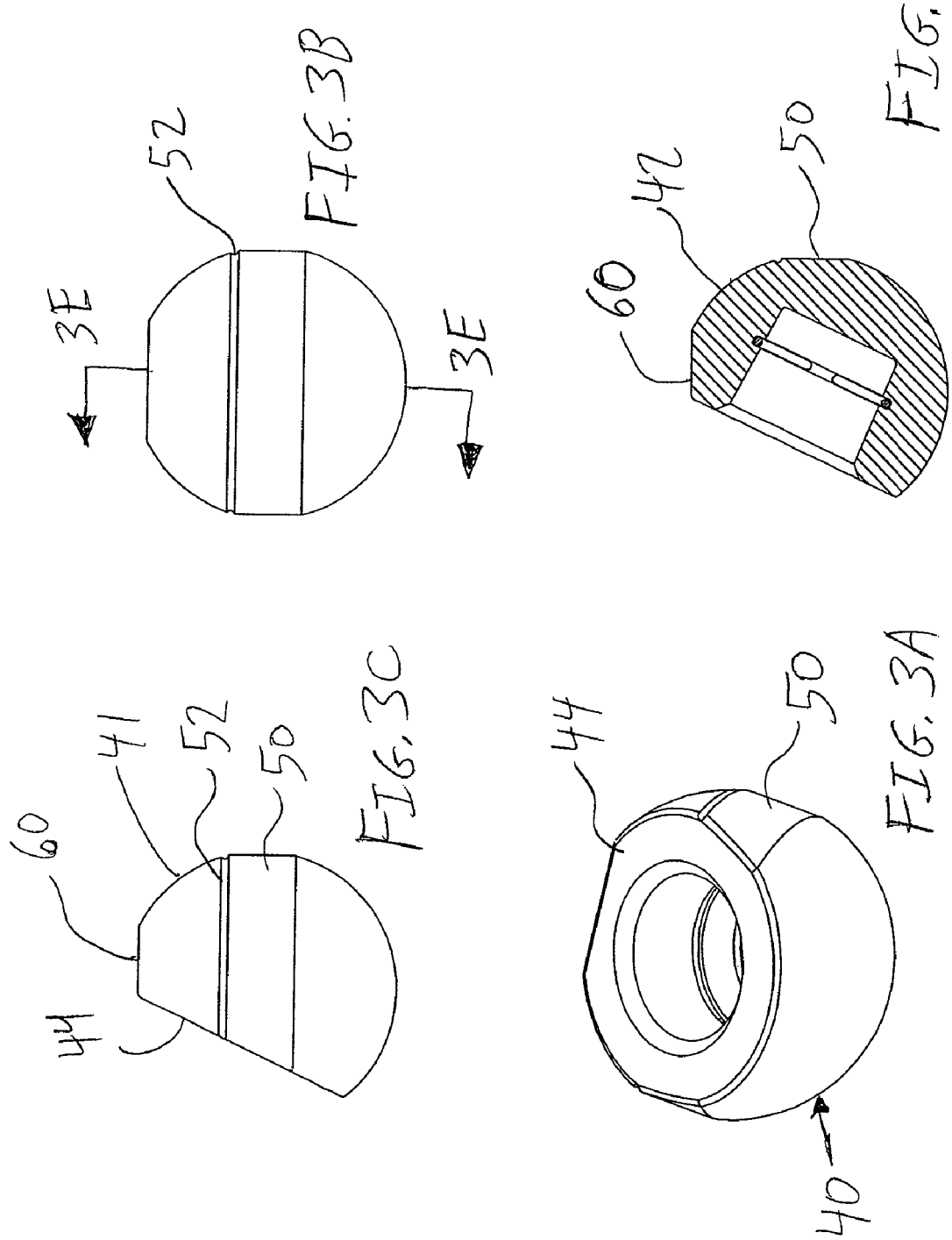

CONSTRAINED ACETABULAR TRIALING SYSTEM

CROSS REFERENCE TO RELATED APPLICATIONS

This application claims priority to U.S. provisional patent application No. 60/863,462, filed Oct. 30, 2006, which is pending.

STATEMENT REGARDING FEDERALLY SPONSORED RESEARCH

Not applicable

FIELD OF THE INVENTION

The present invention relates generally to trialing systems for constrained hip implants, and more particularly to trialing systems for bi-polar hip implants.

BACKGROUND OF THE INVENTION

When implanting hip prostheses, trialing systems are used to verify that the surgeon is using the correct size of shell and head. The present invention provides an improved trialing system for use with constrained hip implants, including particularly bi-polar hip implants. Examples of bi-polar hip implants are found in U.S. Pat. No. 4,241,463 (Khovaylo) and U.S. Pat. No. 4,798,610 (Averill et al.), both of which are incorporated herein by reference.

OBJECTS AND SUMMARY OF THE INVENTION

It is an object of the invention to provide a trialing system for use in implanting a hip prosthesis in a patient.

It is another object of the invention to provide a trialing system that is particularly adapted for use in trialing for a bipolar implant.

It is another object of the invention to provide a trialing system having a locking feature that prevents a trial head from dissociating from a trial shell during trial reduction, yet which readily assembles and disassembles in the operating room.

It is yet another object of the invention to provide a trialing system having a locking feature that prevents a trial head from dissociating from a trial shell during trial reduction, yet which is easy to manufacture, clean and sterilize.

These and other objects and advantages of the invention are achieved by providing a trial head and an associated trial shell having the following characteristics. An outer surface of the trial shell is configured for receipt within the acetabulum. The trial shell has a substantially spherical bearing cavity formed therein for closely receiving the trial head during trial articulation, the bearing cavity extending beyond 180 degrees. The bearing cavity is accessible via a trial shell opening in the trial shell. The trial shell opening includes a head entry portion configured to allow the trial head to pass through the trial shell opening and into the bearing cavity. The head entry portion has a diameter that is less than a diameter of the bearing cavity.

The trial head has a bearing portion and a rim portion. The rim portion is configured to receive a femoral neck during trial articulation. The bearing portion has a substantially spherical outer bearing surface, the bearing surface having a diameter greater than the diameter of the head entry portion of the trial shell opening. A cut-out region is formed in the outer bearing surface. The cut-out region has a diameter that is less than the diameter of the head entry portion of the trial shell opening. The cut-out region is positioned such that when a femoral neck is disposed in the rim portion, the trial head is retained within the bearing cavity of the trial shell. When the cut-out region of the trial head is aligned with the head entry portion of the trial shell opening, the trial head can pass through the trial shell opening and into the bearing cavity of the trial shell. The trial head is retained in the bearing cavity when the cut-out portion is not aligned with the head entry portion.

In a preferred embodiment, the cut-out region is cylindrical and extends along the bearing portion between opposing edges of the rim portion. The cut-out region is preferably obliquely angled relative to the rim of the trial head. The cut-out region is preferably angled at between about 60 and about 70 degrees relative to the rim portion of the trial head, such as at about 65 degrees.

The head entry portion of the trial shell is preferably cylindrical and directly adjacent the bearing cavity. The head entry portion is sized to closely receive the cut-out region of the trial head. The cut-out region is sized to closely pass through the head entry portion of the opening of the trial shell.

An orientation indicator is preferably provided on the trial head. The orientation indicator is positioned to indicate alignment between the cut-out region of the trial head with the head entry portion of the trial shell. In one preferred embodiment, the orientation indicator is a flat formed along the rim portion, the flat being substantially parallel to the cut-out region. An orientation groove can be formed along the cut-out region between the cut-out region and the orientation indicator.

Methods of using the instruments are provided. In one preferred method, a femoral neck is oriented in the femur of the patient for use in trial reduction. A trial head and associated trial shell having the characteristics described herein is provided, such as in the form of a kit having multiple sizes of trial shells and heads. The surgeon aligns the cut-out region of the trial head with the head entry portion of the trial shell opening, inserts the trial head through the trial shell opening and into the shell bearing cavity, and rotates the trial head within the bearing cavity in order to bring the cut-out region out of alignment with the head entry portion. The surgeon inserts the femoral neck into the neck bore of the trial head. The surgeon performs trial reduction on the patient's hip using the trial head and the trial shell. Once trialing is complete, the trial head is removed from trial neck, the cut-out region is rotated back into alignment with the head entry portion of the trial shell opening, and the trial head is removed from the trial shell.

The instruments are provided in the form a surgical kit. The kit may include one or more bipolar hip implants. The kit includes at least one trial head and a plurality of trial shells associated with each trial head for use in trialing for implantation of a selected one of the one or more bipolar hip implants.

The foregoing and other objects, features, aspects and advantages of the invention will become more apparent from the following detailed description of the invention when considered in conjunction with the accompanying drawings.

BRIEF DESCRIPTION OF THE DRAWINGS

FIGS. 2A-2C provide views of one preferred embodiment of a trial shell for use in the invention.

FIGS. 3A-3D provide views of one preferred embodiment of trial head for use in the invention.

PREFERRED EMBODIMENTS OF THE INVENTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1A:
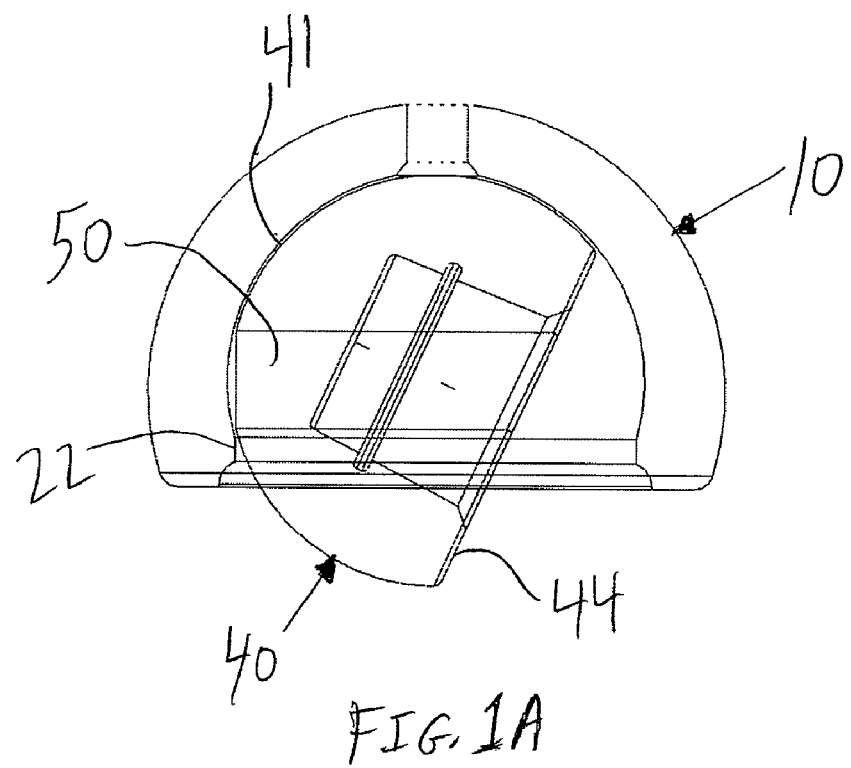
FIG. 1A-1B provide a side view cross-section of one preferred embodiment of a trial shell and trial head of the invention.
Figure 1B:
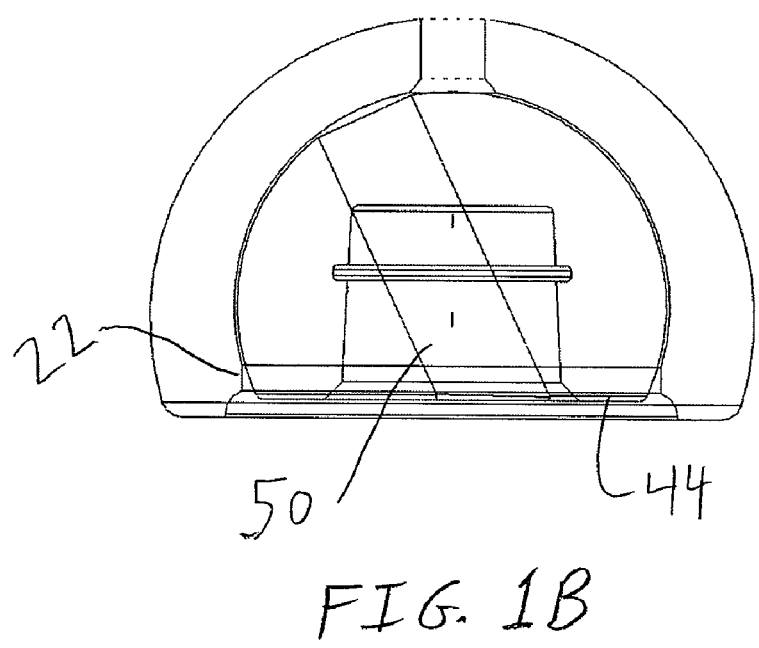

As shown in FIGS. 1A-1B, the invention is a trialing system for use in implanting a hip prosthesis in an acetabulum and a proximal femur of a patient. The trialing system generally comprises a trial shell 10 and an associated trial head 40, with the components having certain characteristics that allow the head 40 and shell 10 to be assembled in one orientation, yet keep the head 40 locked inside the shell 10 during trial articulation. The invention is designed particularly for use with constrained hip implants, and even more particularly for use with constrained bi-polar hip implants such as the type discussed in U.S. Pat. No. 4,241,463 (Khovaylo) and U.S. Pat. No. 4,798,610 (Averill et al.), both of which are incorporated herein by reference.

As indicated in FIG. 2A, an outer surface 14 of the trial shell 10 is configured for receipt within an acetabulum of a patient. For bi-polar shells, the configuration of the outer surface 14 is substantially spherical. As shown in FIG. 2B, the trial shell 10 has a substantially spherical bearing cavity 12 formed therein for closely receiving the trial head 40 during trial articulation. As indicated in the side view cross-section of FIG. 2B, the bearing cavity 12 extends beyond 180 degrees, and preferably to between about 215 and about 220 degrees, with the range preferably selected to closely replicate the degree of constraint of the final acetabular shell implant. As indicated in FIG. 2B, the bearing cavity 12 is accessible via a trial shell opening 20 in the trial shell 10. The trial shell opening 20 includes a head entry portion 22 configured to allow the trial head 40 to pass through the trial shell opening 20 and into the bearing cavity 12, as will be discussed in further detail below. The head entry portion 22 has a diameter that is less than a diameter of the bearing cavity 12.

As indicated in FIG. 3, the trial head 40 has a bearing portion 41 and a rim portion 44. The rim portion 44 is configured to receive a femoral neck during trial articulation, in a manner known to those of skill in the art. The bearing portion 41 has a substantially spherical outer bearing surface 42, the bearing surface 42 having a diameter greater than the diameter of the head entry portion 22 of the trial shell opening 20. The foregoing features of the trial head 40 are known in the art. As shown in FIGS. 1 and 3, the invention improves upon the prior art trial heads by, among other things, providing a cut-out region 50 formed in the outer surface 42. The cut-out region 50 is preferably cylindrical so as to closely match the head entry portion 22 of the trial shell opening 20, although other configurations, such as a concave groove, could be used.

The cut-out region 50 has a diameter that is less than the diameter of trial head 40 and the head entry portion 22 of the trial shell opening 20, a feature that enables the trial head 40 to be inserted into the trial shell 10. The cut-out region 50 is positioned such that when a femoral neck is disposed in the rim portion 44, the trial head 40 is retained within the bearing cavity 12 of the trial shell 10.

As shown in FIG. 1A, when the cut-out region 50 of the trial head 40 is aligned with the head entry portion 22 of the trial shell opening 20 in an assembly orientation, the trial head 40 can pass through the trial shell opening 20 and into the bearing cavity 12 of the trial shell 10. The assembly orientation is outside the normal range of motion of the femoral head, such that the trial head 40 will not disassociate from the trial shell 10 during trial reduction. As shown in FIG. 1B, when the cut-out portion 50 is not aligned with the head entry portion 22, the trial head 40 is retained in the bearing cavity 12. In particular, the spherical diameter of the trial head 40 is too large to allow disassembly past the cylindrical portion 22 of the trial shell 10.

In the embodiment of FIG. 2B, the head entry portion 22 is cylindrical and is directly adjacent the bearing cavity 12. A preferred height of the head entry portion 22 is about 0.2 inches. While the height of the cylinder could have greater or lesser dimensions (including virtually no height), 0.2 inches provides sufficient height to assist with orienting the cut-out region 50 in the opening 20 yet without significantly compromising the articulation characteristics of the trial system during trial articulation. The head entry portion 22 is preferably sized to closely receive the cut-out region 50 of the trial head 40, which serves to optimize the size of the cut-out region 40 and maximize the surface contact between the spherical bearing surface 41 of the trial head 40 and the bearing cavity 12 of the trial shell 10.

The cut-out region 50 could be formed at various orientations and still enable the functionality of the invention. However, when operating within the confines of a hip surgical incision, and particularly the short incisions used in minimally invasive surgical ("MIS") procedures, certain orientations are preferred. The inventors have concluded that the orientation shown in FIGS. 1 and 3 provides optimal performance. As shown in FIG. 3A, the cut-out region 50 preferably extends along the bearing portion between opposing edges of the rim portion 44. As shown in FIG. 3C, the cut-out region 50 is preferably obliquely angled relative to the rim 44 of the trial head 40. In a preferred embodiment, the cut-out region 50 is angled at between about 60 and about 70 degrees relative to the rim portion 44 of the trial head 40, and is most preferably angled at about 65 degrees.

To assist in installing and removing the trial head 40 from the trial shell 10, an orientation indicator 60 is preferably provided on the trial head 40. The orientation indicator 60 is positioned to indicate alignment between the cut-out region 50 of the trial head 40 with the head entry portion 22 of the trial shell 10, such as in the orientation shown in FIG. 1A. As shown in FIGS. 3C and 3D, the orientation indicator 60 is preferably a flat 60 formed along the rim portion 44. As indicated in the side view of FIG. 3C, the flat 60 is preferably substantially parallel to the cut-out region 50. As further indicated in the side view cross-section of FIG. 3D, the depicted configuration allows the surgeon to readily hold the trial head 40 by placing a thumb on the flat 60 and a finger on the underling surface of the bearing cavity 12. Further, due to the placement and orientation of the flat 60 and cut-out region 50, the surgeon can readily insert a finger into the trial neck bore when the trial head 40 is in the assembly orientation in the shell 10, either during insertion or removal of the head 40 from the shell 10. To further assist the surgeon in orientating the trial head 40, particularly during removal of the trial head 40 from the trial shell 10, an orientation groove 52 can be formed along the cut-out region 50. As shown in FIG. 3C, the orientation groove 52 is preferably formed between the cut-out region 50 and the orientation indicator 60.

Figure 5:
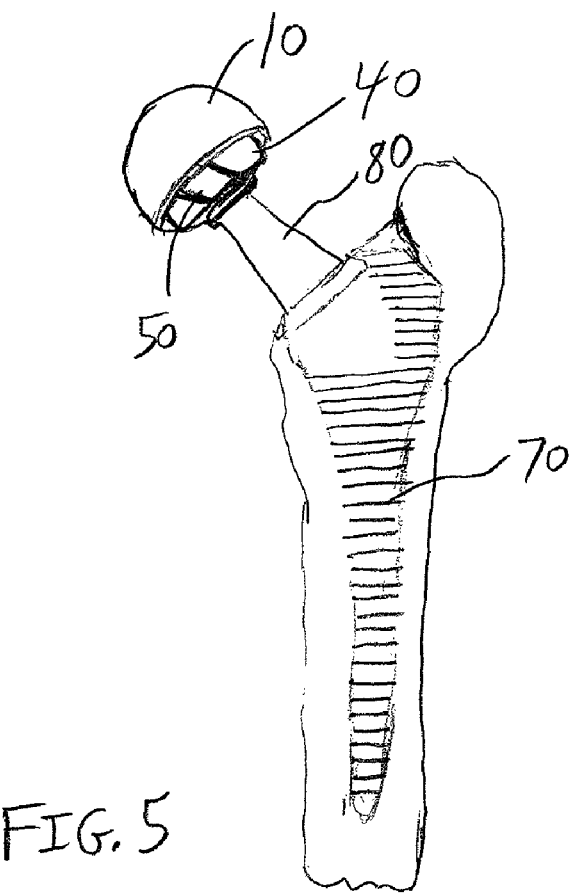
FIG. 5 provides a side view of one preferred embodiment of a trialing system of the invention oriented on a modular femoral neck for use in trial reduction on a patient.

In operation, the trialing system of the invention is used for trial reduction of a bipolar hip implant. As indicated in FIG. 5, the proximal femur is prepared for receipt of an appropriately sized femoral stem 70. A trial femoral stem 70 is positioned in the prepared femur. As indicated in FIG. 5, in a preferred system, the trial femoral stem 70 is configured as a broach having a trial modular neck 80. The use of a trial modular neck provides advantages, such as reduced trial inventory, enhanced trial options, and facilitation of MIS procedures. However, the trialing instruments of the invention can be used with a fixed neck femoral stem trial. The instruments can also be used with a modular or fixed neck implant rather than a femoral trial, for example in a revision surgery.

Figure 4:
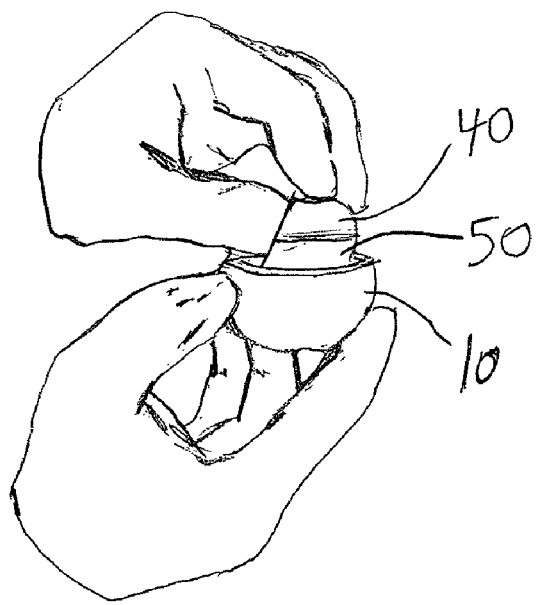
FIG. 4 provides a perspective view of a surgeon using orientation features of one preferred embodiment of the invention in order to insert a trial head into a trial shell for using trial reduction on a patient.

The trialing system is used by orienting the trial shell 10 in the acetabulum of the patient, aligning the cut-out region 50 of the trial head 40 with the head entry portion 22 of the trial shell opening 20, and inserting the trial head 40 through the trial shell opening 20 and into the shell bearing cavity 12 in the assembly orientation, as indicated in FIG. 1A. The trial head 40 is then rotated within the bearing cavity 12 in order to bring the cut-out region 50 out of alignment with the head entry portion 22, as indicated in FIG. 1B. The trial neck 80 of the femoral trial implant is then inserted into the neck bore of the trial head, in a manner known to those of skill in the art. The neck 80 can include a removable sleeve (not shown) on a trial head receiving end of the neck for use in assessing short, medium and long neck options, the sleeve being configured to securely associate with the neck bore of the trial head during trial reduction. As indicated in FIG. 4, in an alternative preferred method, the trial head 40 is placed in the trial shell 10 before placing the trial head and trial shell into the patient. The trial head-trial shell construct 10-40 is then placed onto a femoral neck 80 oriented in the patient's femur.

FIG. 4 provides a perspective view of a surgeon using orientation features of one preferred embodiment of the invention in order to insert or remove a trial head 40 into a trial shell 40 for use in trial reduction on a patient. Due to the orientation of the cut-out region 50, the trial head 40 cannot disassociate from the trial shell 10 while the trial neck is in the trial head 40. This allows the surgeon to perform trial articulation without worrying about disassociation. Once trialing is complete, the surgeon removes the trial neck from the trial head 40 and rotates the cut-out region 50 back into alignment with the head entry portion 22 of the trial shell opening 20, as indicated in FIG. 1A. If orientation indicators, such as the flat 60 and groove 52 of FIG. 3C, are provided, the indicators are used to insert and remove the head 40 from the shell 10.

The components of the trialing system are preferably provided in the form of a surgical kit, the kit having a plurality of different sized trial cups and matching trial heads. The various trial sizes conform to sizes of final hip implants, which can form part of the kit. For example, the kit may include three sizes of trial heads 40 and a plurality of different sized shells 10 associated with each size of trial head 10. The components of the kit are preferably arranged in a convenient format, such as in a surgical tray or case. However, the kit components do not have to be packaged or delivered together, provided that they are assembled or collected together in the operating room for use at the time of surgery.

As used herein, the term "substantially spherical" is intended to include components that are functionally spherical but which deviate from perfect sphericity.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A trialing system for use in implanting a hip prosthesis in an acetabulum and a proximal femur of a patient, the trialing system comprising:
   a trial head and an associated trial shell,
   an outer surface of said trial shell configured for receipt within the acetabulum,
   said trial shell having a substantially spherical bearing cavity formed therein for closely receiving said trial head during trial articulation, said bearing cavity extending beyond 180 degrees,
   said bearing cavity accessible via a trial shell opening in said trial shell, said trial shell opening including a head entry portion configured to allow said trial head to pass through said trial shell opening and into said bearing cavity, said head entry portion having a diameter that is less than a diameter of said bearing cavity,
   said trial head having a bearing portion and a rim portion,
   said rim portion configured to receive a femoral neck during trial articulation, said bearing portion having a substantially spherical outer bearing surface, said bearing surface having a diameter greater than said diameter of said head entry portion of said trial shell opening,
   a cut-out region formed in said outer bearing surface, said cut-out region having a diameter that is less than said diameter of said head entry portion of said trial shell opening, said cut-out region positioned such that when a femoral neck is disposed in said rim portion, said trial head is retained within said bearing cavity of said trial shell, whereby when said cut-out region of said trial head is aligned with said head entry portion of said trial shell opening, said trial head can pass through said trial shell opening and into said bearing cavity of said trial shell, and whereby said trial head is retained in said bearing cavity when said cut-out region is not aligned with said head entry portion, further comprising an orientation indicator on said trial head, said orientation indicator positioned to indicate alignment between said cut-out region of said trial head with said head entry portion of said trial shell, wherein an orientation groove is formed along said cut-out region between said cut-out region and said orientation indicator.

2. A trialing system of claim 1, wherein said cut-out region is cylindrical and extends along said bearing portion between opposing edges of said rim portion.

3. A trialing system of claim 2, wherein said cut-out region is obliquely angled relative to said rim of said trial head.

4. A trialing system of claim 3, wherein said cut-out region is angled at between about 60 and about 70 degrees relative to said rim portion of said trial head.

5. A trialing system of claim 4, wherein said cut-out region is angled at about 65 degrees relative to said rim portion of said trial head.

6. A trialing system of claim 1, wherein said orientation indicator is a flat formed along said rim portion, said flat being substantially parallel to said cut-out region.

7. A trialing system of claim 4, further comprising an orientation indicator on said trial head, said orientation indicator positioned to indicate alignment between said cut-out region of said trial head with said head entry portion of said trial shell.

8. A trialing system of claim 7, wherein said orientation indicator is a flat formed along said rim portion, said flat being substantially parallel to said cut-out region.

9. A trialing system of claim 7, wherein an orientation groove is formed along said cut-out region between said cut-out region and said orientation indicator.

10. A trialing system of claim 1, wherein said head entry portion of said trial shell is cylindrical.

11. A trialing system of claim 10, wherein said head entry portion is directly adjacent said bearing cavity.

12. A trialing system of claim 10, wherein a height of said head entry portion is about 0.2 inches.

13. A trialing system of claim 10, wherein said head entry portion is sized to closely receive said cut-out region of said trial head.

14. A trialing system of claim 1, wherein said bearing cavity of said trial shell extends between about 215 and about 220 degrees.

15. A trialing system of claim 1, wherein said cut-out region is sized to closely pass through said head entry portion of said opening of said trial shell.

16. A method of trialing for a bi-polar hip implant in an acetabulum and a proximal femur of a patient comprising:
orienting a femoral neck in the femur of the patient for use in trial reduction,
providing a trial head and an associated trial shell, said trial head and said associated trial shell comprising
an outer surface of said trial shell configured for receipt within the acetabulum,
said trial shell having a substantially spherical bearing cavity formed therein for closely receiving said trial head during trial articulation, said bearing cavity extending beyond 180 degrees,
said bearing cavity accessible via a trial shell opening in said trial shell, said trial shell opening including a head entry portion configured to allow said trial head to pass through said trial shell opening and into said bearing cavity, said head entry portion having a diameter that is less than a diameter of said bearing cavity,
said trial head having a bearing portion and a rim portion,
said rim portion configured to receive a femoral neck during trial articulation,
said bearing portion having a substantially spherical outer bearing surface, said bearing surface having a diameter greater than said diameter of said head entry portion of said trial shell opening, a cut-out region formed in said outer bearing surface,
said cut-out region having a diameter that is less than said diameter of said head entry portion of said trial shell opening, said cut-out region positioned such that when a femoral neck is disposed in said rim portion, said trial head is retained within said bearing cavity of said trial shell, whereby when said cut-out region of said trial head is aligned with said head entry portion of said trial shell opening, said trial head can pass through said trial shell opening and into said bearing cavity of said trial shell, and whereby said trial head is retained in said bearing cavity when said cut-out region is not aligned with said head entry portion,
aligning said cut-out region of said trial head with said head entry portion of said trial shell opening, inserting said trial head through said trial shell opening and into said shell bearing cavity, rotating said trial head within said bearing cavity in order to bring said cut-out region out of alignment with said head entry portion, securing said trial head on said femoral neck via said neck bore of said trial head, and performing trial reduction on the patient's hip using said trial head and said trial shell.

17. The method of claim 16, further comprising, once trialing is complete, dissociating said trial head from said trial neck, rotating said cut-out region back into alignment with said head entry portion of said trial shell opening, and removing said trial head from said trial shell.

18. The method of claim 16, wherein said trial shell is oriented in the acetabulum of the patient prior to inserting said trial head in said trial shell.

19. The method of claim 16, wherein said trial head is placed in said trial shell to form a trial head-trial shell assembly before placing said trial head and said trial shell into the patient.

20. The method of claim 16, wherein the femoral neck is modular.

21. The method of claim 20, wherein the modular femoral neck is a trial modular neck.

22. A surgical kit including a trialing system for a bipolar hip implant for a patient comprising:
one or more bipolar hip implants, each said bipolar hip implant comprising a femoral stem, a bipolar acetabular shell, and a bipolar head,
at least one trial head and a plurality of trial shells associated with each said trial head for use in trialing for implantation of a selected one of said one or more bipolar hip implants,
each said trial shell comprising
an outer surface of said trial shell configured for receipt within the acetabulum,
said trial shell having a substantially spherical bearing cavity formed therein for closely receiving said trial head during trial articulation, said bearing cavity extending beyond 180 degrees,
said bearing cavity accessible via a trial shell opening in said trial shell, said trial shell opening including a head entry portion configured to allow said trial head to pass through said trial shell opening and into said bearing cavity, said head entry portion having a diameter that is less than a diameter of said bearing cavity,
each said trial head comprising said trial head having a bearing portion and a rim portion,
said rim portion configured to receive a femoral neck during trial articulation,
said bearing portion having a substantially spherical outer bearing surface, said bearing surface having a diameter greater than said diameter of said head entry portion of said trial shell opening,
a cut-out region formed in said outer bearing surface, said cut-out region having a diameter that is less than said diameter of said head entry portion of said trial shell opening of said associated trial shells, said cut-out region positioned such that when a femoral neck is disposed in said rim portion, said trial head is retained within said bearing cavity of said trial shell, whereby when said cut-out region of said trial head is aligned with said head entry portion of said trial shell opening, said trial head can pass through said trial shell opening and into said bearing cavity of said trial shell, and whereby said trial head is retained in said bearing cavity when said cut-out region is not aligned with said head entry portion.

* * * * *